US007192629B2

(12) United States Patent  
Lammertink et al.

(10) Patent No.: US 7,192,629 B2
(45) Date of Patent: Mar. 20, 2007

(54) DEVICES UTILIZING SELF-ASSEMBLED GEL AND METHOD OF MANUFACTURE

(75) Inventors: Rob G. H. Lammertink, Nijverdal (NL); Todd Thorsen, Watertown, MA (US); Stephen R. Quake, San Marino, CA (US); Julia A. Kornfield, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 33 days.

(21) Appl. No.: 10/269,475

(22) Filed: Oct. 11, 2002

(65) Prior Publication Data

US 2003/0134129 A1    Jul. 17, 2003

Related U.S. Application Data

(60) Provisional application No. 60/328,595, filed on Oct. 11, 2001.

(51) Int. Cl.  
 B29D 23/00  (2006.01)

(52) U.S. Cl. .................... 428/36.9; 428/447; 428/35.7; 210/198.2; 210/656; 96/101

(58) Field of Classification Search ............. 428/36.9, 428/447, 35.7; 210/656, 198.2; 96/101  
See application file for complete search history.

(56) References Cited

U.S. PATENT DOCUMENTS

| 3,570,515 | A | 3/1971 | Kinner |
| 3,747,628 | A | 7/1973 | Holster et al. |
| 4,046,159 | A | 9/1977 | Pegourie |
| 4,119,368 | A | 10/1978 | Yamakazi |
| 4,153,855 | A | 5/1979 | Feingold |
| 4,245,673 | A | 1/1981 | Bouteille et al. |
| 4,373,527 | A | 2/1983 | Fischell |
| 4,434,704 | A | 3/1984 | Surjaatmadja |
| 4,575,681 | A | 3/1986 | Grosso et al. |
| 4,662,710 | A | 5/1987 | ten Berge |
| 4,898,582 | A | 2/1990 | Faste |
| 4,992,312 | A | 2/1991 | Frisch |
| 5,085,562 | A | 2/1992 | Van Lintel |
| 5,088,515 | A | 2/1992 | Kamen |
| 5,096,388 | A | 3/1992 | Weinberg |
| 5,126,115 | A | 6/1992 | Fujita et al. |
| 5,164,558 | A | 11/1992 | Huff et al. |
| 5,171,132 | A | 12/1992 | Miyazaki |
| 5,224,843 | A | 7/1993 | Van Lintel |
| 5,259,737 | A | 11/1993 | Kamisuki et al. |
| 5,265,327 | A | 11/1993 | Faris et al. |
| 5,290,240 | A | 3/1994 | Horres, Jr. |
| 5,336,062 | A | 8/1994 | Richter |
| 5,346,372 | A | 9/1994 | Naruse et al. |
| 5,375,979 | A | 12/1994 | Trah |
| 5,376,252 | A | 12/1994 | Ekstrom |
| 5,400,741 | A | 3/1995 | DeTitta et al. |
| 5,423,287 | A | 6/1995 | Usami et al. |
| 5,529,465 | A | 6/1996 | Zengerle et al. |
| 5,574,893 | A | 11/1996 | Southgate et al. |
| 5,593,130 | A | 1/1997 | Hansson et al. |
| 5,642,015 | A | 6/1997 | Whitehead et al. |
| 5,659,171 | A | 8/1997 | Young et al. |
| 5,660,370 | A | 8/1997 | Webster |
| 5,665,070 | A | 9/1997 | McPhee |
| 5,681,024 | A | 10/1997 | Lisec et al. |
| 5,705,018 | A | 1/1998 | Hartley |
| 5,759,014 | A | 6/1998 | Van Lintel |
| 5,775,371 | A | 7/1998 | Pan et al. |
| 5,788,468 | A | 8/1998 | Dewa et al. |
| 5,836,750 | A | 11/1998 | Cabuz |
| 5,842,787 | A | 12/1998 | Kopf-Sill et al. |
| 5,854,684 | A | 12/1998 | Stabile et al. |
| 5,875,817 | A | 3/1999 | Carter |
| 5,876,187 | A | 3/1999 | Forster et al. |
| 5,932,799 | A | 8/1999 | Moles |
| 5,942,443 | A | 8/1999 | Parce et al. |
| 5,997,961 | A | 12/1999 | Feng et al. ................. 427/515 |
| 6,007,309 | A | 12/1999 | Hartley |
| 6,043,080 | A | 3/2000 | Lipshutz et al. |

(Continued)

FOREIGN PATENT DOCUMENTS

| EP | 0 592 094 A2 | 4/1994 |
| EP | 0 703 364 A1 | 3/1996 |
| EP | 0 706 004 A2 | 4/1996 |
| EP | 0 779 436 A2 | 6/1997 |
| EP | 0 829 360 A2 | 3/1998 |

(Continued)

OTHER PUBLICATIONS

"Biochips," Nature Biotechnology, vol. 18, Supplement 2000, pp. IT43-IT44, 2000.  
"Chapter 9: Microfluidic Devices," Micromachined Transducers Sourcebook, pp. 779-882, 1998.  
"Last Chance For Micromachines," The Economist Technology Quarterly, 8 pages, Dec. 7, 2000.  
Ahn, Chong H. et al., "Fluid Micropumps Based on Rotary Magnetic Actuators," Proceedings of 1995 IEEE Micro Electro Mechanical Systems Workshop (MEMS '95), Amsterdam, Netherlands, pp. 408-412, Jan. 29-Feb. 2, 1995.

(Continued)

Primary Examiner—Margaret G. Moore  
(74) Attorney, Agent, or Firm—Townsend and Townsend and Crew LLP

(57) ABSTRACT

Devices such as capillaries for capillary electrophoresis are formed by contacting a gel precursor with a substrate comprising a permeable material that has higher permeability for organic solvents than water. The gel precursor is made of a water soluble polymer having hydrophobic moieties in a solvent mixture comprising water and an organic solvent, wherein in the absence of the organic solvent, the polymer forms a self-assembled gel. The organic solvent is allowed to permeate through the permeable material resulting in the formation of the self-assembled gel.

11 Claims, 1 Drawing Sheet

U.S. PATENT DOCUMENTS

| | | | |
|---|---|---|---|
| 6,123,769 A | 9/2000 | Sanjoh | |
| 6,155,282 A | 12/2000 | Zachary et al. | |
| 6,174,365 B1 | 1/2001 | Sanjoh | |
| 6,246,330 B1 | 6/2001 | Nielsen | |
| 6,296,673 B1 | 10/2001 | Santarsiero et al. | |
| 6,329,209 B1 | 12/2001 | Wagner et al. | 436/518 |
| 6,345,502 B1 | 2/2002 | Tai et al. | |
| 6,358,387 B1 | 3/2002 | Kopf-Sill et al. | |
| 6,375,871 B1 | 4/2002 | Bentsen et al. | |
| 6,376,971 B1 | 4/2002 | Petrine et al. | |
| 6,409,832 B2 | 6/2002 | Weigl et al. | |
| 6,488,832 B2 | 12/2002 | Heller | 204/603 |
| 6,488,872 B1 | 12/2002 | Beebe et al. | 264/31 |
| 6,520,936 B1 | 2/2003 | Mann | |
| 6,541,071 B1* | 4/2003 | Bookbinder et al. | 427/407.2 |
| 6,667,124 B2 | 12/2003 | Suenaga et al. | |
| 6,689,473 B2* | 2/2004 | Guire et al. | 428/412 |
| 6,716,378 B2* | 4/2004 | Yang et al. | 264/42 |
| 6,767,706 B2 | 7/2004 | Quake et al. | |
| 6,829,753 B2 | 12/2004 | Lee et al. | |
| 6,847,153 B1 | 1/2005 | Balizer | |
| 6,866,785 B2* | 3/2005 | Zare et al. | 210/656 |
| 6,884,346 B2* | 4/2005 | Zare et al. | 210/198.2 |
| 2001/0027745 A1 | 10/2001 | Weigl et al. | |
| 2002/0014673 A1 | 2/2002 | Leedy | |
| 2002/0037499 A1 | 3/2002 | Quake et al. | |
| 2002/0045297 A1 | 4/2002 | Leedy | |
| 2002/0108096 A1 | 8/2002 | Lee et al. | |
| 2003/0080442 A1 | 5/2003 | Unger | |
| 2004/0072278 A1 | 4/2004 | Chou et al. | |
| 2004/0248167 A1 | 12/2004 | Quake et al. | |
| 2005/0065735 A1 | 3/2005 | Lee et al. | |
| 2005/0197652 A1 | 9/2005 | Nat | |

FOREIGN PATENT DOCUMENTS

| | | |
|---|---|---|
| EP | 0 845 603 A1 | 6/1998 |
| EP | 0 999 055 A2 | 5/2000 |
| GB | 2 155 152 A | 9/1985 |
| GB | 2 308 460 A | 6/1997 |
| WO | WO 98/07069 A1 | 2/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 00/00678 A1 | 1/2000 |
| WO | WO 00/43748 A1 | 7/2000 |
| WO | WO 00/60345 A1 | 10/2000 |
| WO | WO 01/06529 A1 | 1/2001 |
| WO | WO 01/06575 A1 | 1/2001 |
| WO | WO 01/09595 A2 | 2/2001 |
| WO | WO 01/09595 A3 | 2/2001 |
| WO | WO 02/82047 A2 | 10/2002 |

OTHER PUBLICATIONS

Anderson, Janelle R. et al., "Fabrication of Topologically Complex Three-Dimensional Microfluidic Systems in PDMS by Rapid Prototyping," Analytical Chemistry, vol. 72, No. 14, pp. 3158-3164, Jul. 15, 2000.
Anderson, Rolfe C. et al., "Microfluidic Biochemical Analysis System," Tranducers '97, 1997 International Conference on Solid-State Sensors and Actuators, Chicago, Illinois, pp. 477-480, Jun. 16-19, 1997.
Angell, James B. et al., "Silicon Micromechanical Devices," Scientific American, pp. cover, 44-55, Apr. 1983.
Armani, Deniz et al., "Re-Configurable Fluid Circuits By PDMAS Elastomer Micromachining," IEEE Int. Conf. Micro Electro Mech. Syst. Tech. Digest, vol. 12, pp. 222-227, 1999.
Ballantyne, J. P. et al., "Selective Area Metallization By Electron-Bearn Controlled Direct Metallic Deposition," J. Vac. Sci. Technol., vol. 10, No. 6, pp. 1094-1097, Nov. 1973.
Benard, W. L. et al., "A Titanium-Nickel Shape-Memory Alloy Actuated Micropump," Transducers '97, 1997 International Conference on Solid-State Sensors and Actuators, Chicago, Illinois, pp. 361-364, Jun. 16-19, 1997.
Black, Harvey, "Tiny Technology Promises Tremendous Profits," The Scientist, vol. 15, No. 21, 4 pages, Oct. 29, 2001.
Bloomstein, T. M. et al., "Laser-Chemical Three-Dimensional Writing For Microelectromechanics And Application to Standard-Cell Microfluidics," J. Vac. Sci. Technol. B, vol. 10, No. 6, pp. 2671-2674, Nov. 1992.
Bousse, Luc et al., "Electrokinetically Controlled Microfluidic Anaylsis Systems," Annu. Rev. Biophys. Biomol. Struct., vol. 29, pp. 155-181, 2000.
Brechtel, R. et al., "Control Of The Electroosmotic Flow By Metal-Salt-Containing Buffers," Journal of Chromatography A, vol. 716, pp. 97-105, 1995.
Bryzek, Janusz et al., "Micromachines On The March", IEEE Spectrum, vol. 31, No. 5, pp. 20-31, May 1994.
Buchaillot, Lionel et al., "Silicon Nitride Thin Films Young's Modulus Determination By An Optical Non Destructive Method," Jpn. J. Appl. Phys., vol. 36, Part 2, No. 6B, pp. L794-L797, Jun. 15, 1997.
Calkins, Kathryn, "Mycometrix: Rubber Chips," BioCentury, 2 pages, Oct. 16, 2000.
Chan, Jason H. et al., "Microfabricated Polymer Devices For Automated Sample Delivery of Peptides For Analysis By Electrospray Ionization Tandem Mass Spectrometry," Analytical Chemistry, vol. 71, No. 20, pp. 4437-4444, Oct. 15, 1999.
Chiang, Yuh-Min et al., "Characterizing The Process of Cast Molding Microfluidic Systems," SPIE, vol. 3877, pp. 303-311, Sep. 1999.
Chiu, Daniel T. et al., "Patterned Deposition of Cells and Proteins Onto Surfaces By Using Three-Dimensional Microfluidic Systems," PNAS, vol. 97, No. 6, pp. 2408-2413, Mar. 14, 2000.
Chou, Hou-Pu et al., "A Microfabricated Device For Sizing And Sorting DNA Molecules," Proc. Natl. Acad. Sci., vol. 96, pp. 11-13, Jan. 1999.
Chou, Hou-Pu et al., "A Microfabricated Rotary Pump," Biomedical Microdevices, vol. 3, No. 4, pp. 323-330, 2001.
Chou, Hou-Pu et al., "Integrated Elastomer Fluidic Lab-On-A-Chip-Surface Patterning and DNA Diagnostics," Proceedings of the Solid State Actuator and Sensor Workshop, Hilton Head. South Carclina, 4 pages, 2000.
Chou, Hou-Pu et al., "Multiple Disease Diagnostics on a Single Chip," Biophysics Lab. Caltech, pp. 1-4, Mar. 1, 2000.
Delamarche, Emmanuel et al., "Patterned Delivery of Immunoglobulins to Surfaces Using Microfluidic Networks," Science, vol. 276, pp. 779-781, May 2, 1997.
Dharmatilleke, Saman et al., "Three-Dimensional Silicone Device Fabrication and Interconnection Scheme For Microfluidic Applications Using Sacrificial Wax Layers," Micro-Electro-Mechanical Systems (MEMS), vol. 2, pp. 413-418, 2000.
Duffy, David C. et al., "Patterning Electroluminescent Materials With Feature Sizes as Small as 5μm Using Elastomeric Membranes as Masks for Dry Lift-Off," Advanced Materials, vol. 11, No. 7, pp. 546-552, 1999.
Duffy, David C. et al., "Rapid Prototyping of Microfluidic Switches in Poly(dimethyl siloxane) And Their Actuation By Electro-Osmotic Flow," J. Micromech. Microeng., vol. 9, pp. 211-217, 1999.
Duffy, David C. et al., "Rapid Prototyping of Microfluidic Systems in Poly(dimethylsiloxane)," Analytical Chemistry, vol. 70, No. 23, pp. 4974-4984, Dec. 1, 1998.
Effenhauser, Carlo S. et al., "Integrated Chip-Based Capillary Electophoresis," Electrophoresis, vol. 18, pp. 2203-2213, 1997.
Ericson, Christer et al., "Electroosmosis- And Pressure-Driven Chromatography In Chips Using Continuous Beds," Analytical Chemistry, vol. 72, No. 1, pp. 81-87, Jan. 1, 2000.
Eyal, Shulamit et al., "Velocity-Independent Microfluidic Flow Cytometry," Electrophoresis, vol. 23, pp. 2653-2657, 2002.
Fahrenberg, J. et al., "A Microwave System Fabricated By Thermoplastic Molding," J. Micromech. Microeng., vol. 5, pp. 169-171, 1995.

Fettinger, J. C. et al., "Stacked Modules For Micro Flow Systems In Chemical Analysis: Concept And Studies Using An Enlarged Model," Sensors and Actuators B, vol. 17, pp. 19-25, 1993.

Figeys, Daniel et al., "An Integrated Microfluidics-Tandem Mass Spectrometry System For Automated Protein Analysis," Analytical Chemistry, vol. 70, No. 18, pp. 3728-3734, Sep. 15, 1998.

Figeys, Daniel et al., "Nanoflow Solvent Gradient Delivery From A Microfabricated Device For Protein Identifications By Electrospray Ionization Mass Spectrometry," Analytical Chemistry, vol. 70, No. 18, pp. 3721-3727, Sep. 15, 1998.

Fitzgerald, Deborah A., "Making Every Nanoliter Count," The Scientist, vol. 15, No. 21, 8 pages, Oct. 29, 2001.

Folch, A. et al., "Molding Of Deep Polydimethylsiloxane Microstructures For Microfluidics And Biological Applications," Journal of Biomechanical Engineering, vol. 121, pp. 28-34, Feb. 1999.

Fu, Anne Y. et al., "A Microfabricated Fluorescence-Activated Cell-Sorter," Nature Biotechnology, vol. 17, pp. 1109-1111, Nov. 1999.

Galambos, Paul et al., "Electrical And Fluidic Packaging Of Surface Micromachined Electro-Microfluidic Devices," 8 pages, no date.

Gao, Jun et al., "Integrated Microfluidic System Enabling Protein Digestion, Peptide Separation, And Protein Identification," Analytical Chemistry, vol. 73, No. 11, pp. 2648-2655, Jun. 1, 2001.

Garno, Jayne C. et al., "Production Of Periodic Arrays Of Protein Nanostructures Using Particle Lithography," Langmuir, vol. 18, No. 21, pp. 8186-8192, 2002.

Gass, V. et al., "Integrated Flow-Regulated Silicon Micropump," Sensors and Actuators A, vol. 43, pp. 335-338, 1994.

Gerlach, Torsten, "Pumping Gases By A Silicon Micro Pump With Dynamic Passive Valves," Transducers '97, 1997 International. Conference on Solid-State Sensors and Actuators, Chicago, Illinois, pp. 357-360, Jun. 16-19, 1997.

Goll, C. et al., "Microvalves With Bistable Buckled Polymer Diaphragms," J. Micromech. Microeng., vol. 6, pp. 77-79, 1996.

Gravesen, Peter et al., "Microfluidics-A Review," J. Micromech. Microeng., vol. 3, pp. 168-192, 1993.

Greene, Chana, "Characterizing The Properties Of PDMS," pp. 1-11, Summer 2000.

Guërin, L. J. et al., "Simple And Low Cost Fabrication Of Embedded Micro-Channels By Using A New Thick-Film Photoplastic," Transducers '97, 1997 International Conference on Solid-State Sensors and Actuators, Chicago, Illinois, pp. 1419-1422, Jun. 18-19, 1997.

Harrison, D. Jed et al., "Micromachining A Miniaturized Capillary Electrophoresis-Based Chemical Analysis System On A Chip," Science, vol. 261, pp. 895-897, Aug. 13, 1993.

Henion, Jack et al., "Capillary Electrophoresis/Mass Spectrometry: From One Meter Capillaries To Chip-Based Devices," 2 pages, 1999.

Hicks, Jennifer, "Genetics And Drug Discovery Dominate Microarray Research," R&D Magazine, pp. 28-33, Feb. 1999.

Hofmann; Oliver et al., "Modular Approach To Fabrication Of Three-Dimensional Microchannel Systems in PDMS—Application To Sheath Flow Microchips," Labs on a Chip, vol. 1, pp. 108-114, 2001.

Hopfgartner, Gerard et al., "Exact Mass Measurement Of Product Ions For The Structural Elucidation Of Drug Metabolites With A Tandem Quadrupole Orthogonal-Acceleration Time-Of-Flight Mass Spectrometer," Journal of The American Society for Mass Spectrometry, vol. 10, pp. cover, 1305-1314, Dec. 1999.

Horn, Howard, "Lab Chips Sector: Microtechnologies Are Changing Healthcare And More," Life Sciences, pp. 19-21, Mar. 20, 2001.

Hornbeck, Larry J. et al., "Bistable Deformable Mirror Device," Spatial Light Modulators and Applications 1988 Technical Digest Series, Summaries of papers presented at the Spatial Light Modulators and Applications Topical Meeting, Optical Society of America, vol. 8, Postconference Edition, A215, pp. 107-110, Jun. 15-17, 1988.

Hosokawa, Kazuo et al., "Droplet-Based Nano/Picoliter Mixer Using Hydrophobic Microcapillary Vent," 1999 IEEE International Conference on Micro Electro Mechanical Systems, Technical Digest, pp. 388-393, 1999.

Hosokawa, Kazuo et al., "Handling Of Picoliter Liquid Samples In A Poly(dimethylsiloxane)-Based Microfluidic Device," Analytical Chemistry, vol. 71, No. 20, pp. 4781-4785, Oct. 15, 1999.

Ikuta, Koji et al., "Three Dimensional Micro Integrated Fluid Systems (MIFS) Fabricated By Stereo Lithography," IEEE, pp. 1-6, 1994.

Jacobson, Stephen C. et al., "High-Speed Separations On A Microchip," Analytical Chemistry, vol. 66, No. 7, pp. 1114-1118, Apr. 1, 1994.

Jacobson, Stephen C. et al., "Microfluidic Devices For Electrokinetically Driven Parallel And Serial Mixing," Analytical Chemistry, vol. 71, No. 20, pp. 4455-4459, Oct. 15, 1999.

Jerman, Hal, "Electrically-Activated, Normally-Closed Diaphragm Valves," Transducers '91, 1991 International Conference on Solid-State Sensors and Actuators, pp. cover, 1045-1048. 1991.

Jo, Byung-Ho et al., "Fabrication Of Three-Dimensional Microfluidic Systems By Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication In Polydimethylsiloxane (PDMS) Elastomer," Journal of Microelectromechanical Systems, vol. 9, No. 1, pp. 76-81, Mar. 2000.

Jung, D. R. et al., "Chemical And Physical Interactions At Metal/ Self-Assembled Organic Monolayer Interfaces," pp. 1-54, 1994.

Kagan, C. R., "Organic-Inorganic Hybrid Materials As Semiconducting Channels In Thin-Film Field-Effect Transistors," Science, vol. 286, pp. 945-947, Oct. 29, 1999.

Kapur, Ravi et al., "Fabrication And Selective Surface Modification Of 3-Dimensionally Textured Biomedical Polymers From Etched Silicon Substrates." Journal of Biomedical Materials Research, vol. 33, pp. 205-216, 1996.

Kawano, Yasushi et al., "Rapid Isolation And Identification Of Staphylococcal Exoproteins By Reverse Phase Capillary High Performance Liquid Chromatography-Electrospray Ionization Mass Spectrometry," FEMS Microbiology Letters, vol. 189, pp. 103-108, 2000.

Kenis, Paul J. A. et al., "Microfabrication Inside Capillaries Using Multiphase Laminar Flow Patterning." Science, vol. 285, pp. 83-85, Jul. 2, 1999.

Khoo, Melvin et al., "A Novel Micromachined Magnetic Membrane Microfluid Pump," pp. 1-4, no date.

Kim, Enoch et al., "Micromolding In Capillaries: Applications In Materials Science," J. Am. Chem. Soc., vol. 118, No. 24, pp. 5722-5731, 1996.

Kim, Enoch et al., "Polymer Microstructures Formed By Moulding in Capillaries," Nature, vol. 376, pp. 581-584, Aug. 17, 1995.

Kirk-Othmer, "Concise Encyclopedia of Chemical Technology," John Wiley & Sons, 5 pages, no date.

Kopp, Martin U. et al., "Chemical Amplification: Continuous-Flow PCR On A Chip," Science, vol. 280, pp. 1046-1048, May 15, 1998.

Kuhn, Lawrence et al., "Silicon Charge Electrode Array For Ink Jet Printing," IEEE Transactions on Electron Devices, vol. ED-25, No. 10, pp. 1257-1260. Oct. 1978.

Kumar, Amit et al., "Features Of Gold Having Micrometer To Centimeter Dimensions Can Be Formed Through A Combination Of Stamping With An Elastomeric Stamp And An Alkanethlol 'Ink' Followed By Chemical Etching," Appl. Phys. Lett., vol. 83, No. 14, pp. 2002-2004, Oct. 4, 1993.

Kumar, Amit et al., "Patterning Self-Assembled Monolayers: Applications In Materials Science," Langmuir, vol. 10, pp. 1498-1511, 1994.

Lagally, Eric T. et al., "Fully Integrated PCR-Capillary Electrophoresis Microsystem For DNA Analysis," Lab On A Chip, vol. 1, pp. 102-107, 2001.

Lagally, Eric T. et al., "Monolithic Integrated Microfluidic DNA Amplification And Capillary Electrophoresis Anaylsis System," Sensors and Actuators B, vol. 63, pp. 138-146, 2000.

Lagally, E. T. et al., "Single-Molecule DNA Amplification And Analysis In An Integrated Microfluidic Device," Analytical Chemistry, vol. 73, No. 3, pp. 565-570, Feb. 1, 2001.

Lammerink, T. S. J. et al., "Modular Concept For Fluid Handling Systems," IEEE, pp. 389-394, 1996.

Lazar, Iulia M. et al., "Novel Microfabricated Device For Electrokinetically Induced Pressure Flow And Electrospray Ionization Mass Spectrometry," Journal of Chromatography A, vol. 892, pp. 195-201, 2000.

Li, Jianjun et al., "Integration Of Microfabricated Devices To Capillary Electrophoresis-Electrospray Mass Spectrometry Using A Low Dead Volume Connection: Application To Rapid Analyses Of Proteolytic Digests," Analytical Chemistry, vol. 71, No. 15, pp. 3036-3045, Aug. 1, 1999.

Li, Paul C. H. et al., "Transport Manipulation, And Reaction Of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source For Mass Spectrometry," Analytical Chemistry, vol. 72, No. 2, pp. 367-375, Jan. 15, 2000.

Lin, L. Y. et al., "Free-Space Micromachined Optical Switches For Optical Networking," IEEE Journal of Selected Topics in Quantum Electronics, vol. 5, No. 1, pp. 4-9, Jan. 1999.

Lin, Yuehe et al., "Laser Micromachined Isoelectric Focusing Device On Polymer Substrate For Electrospray Mass Spectrometry," SPIE, vol. 3877, pp. 28-35, Sep. 1999.

Liu, Hanghui et al., "Development Of Multichannel Devices With An Array Of Electrospray Tips For High-Throughput Mass Spectrometry," Analytical Chemistry, vol. 72, No. 14, pp. 3303-3310, Jul. 15, 2000.

Liu, Jian et al., "A Nanoliter Rotary Device For Polymerase Chain Reaction," Electrophoresis, vol. 23, pp. 1531-1536, 2002.

Lötters, J C et al., "The Mechanical Properties Of The Rubber Elastic Polymer Polydimethylsiloxane For Sensor Applications," J. Micromech. Microeng., vol. 7, pp. 145-147, 1997.

Lucy, Charles A. et al., "Characterization Of The Cationic Surfactant Induced Reversal Of Electroosmotic Flow In Capillary Electrophoresis," Anal. Chem., vol. 68, pp. 300-305, 1996.

Maluf, N., "An Introduction To Microelectromechanical Systems Engineering," Artech House Publishers, Boston London, pp. 42-45, Dec. 1999.

Manz, A. et al., "Micromachining Of Monocrystalline Silicon And Glass For Chemical Analysis Systems," Trends in Analytical Chemistry, vol. 10, No. 5, pp. 144-149, 1991.

Marshall, SID, "Fundamental Changes Ahead For Lab Instrumentation," R&D Magazine, 5 pages, Feb. 1999.

Marsili, Ray, "Lab-On-A-Chip Poised To Revolutionize Sample Prep," R&D Magazine, 5 pages, Feb. 1999.

Maule, John, "Pulsed-Field Gel Electrophoresis," Molecular Biotechnology, vol. 9, pp. 107-126, 1998.

McDonald, J. Cooper et al., "Fabrication Of Microfluidic Systems In Poly(dimethylsiloxane)," Electrophoresis, vol. 21, pp. 27-40, 2000.

McDonald, J. Cooper et al., "Poly(dimethylsiloxane) As A Material For Fabricating Microfluidic Devices," Accounts of Chemical Research, vol. 35, No. 7, pp. 491-499, 2002.

Muller, Richard S. et al., "Surface-Micromachined Microoptical Elements And Systems," Proceedings of the IEEE, vol. 86, No. 8, pp. 1705-1720, Aug. 1998.

New Objective, Inc., "What Is Electrospray," www.newobjective.com/electrospray/electrospray.html, 4 pages, 1999.

Ng, Jessamine M. K. et al., "Components For Integrated Poly(Dimethylsiloxane) Microfluidic Systems," Electrophoresis, vol. 23, pp. 3461-3473, 2002.

Oleschuk, Richard D. et al., "Analytical Microdevices For Mass Spectrometry," Trends in Analytical Chemistry, vol. 19, No. 6., pp. 379-388, 2000.

Olsson, Anders et al., "Simulation Studies Of Diffuser And Nozzle Elements For Valve-Less Micropumps." Transducers '97, 1997 International Conference on Solid-State Sensors and Actuators, Chicago, Illinois, pp. 1039-1042, Jun. 16-19, 1997.

O'Reilly, Marie-Anne J. et al., "The Technique Of Pulsed Field Gel Electrophoresis And Its Impact On Molecular Immunology," Journal of Immunological Methods, vol. 131, pp. 1-13, 1990.

Pethig, Ronald et al., "Applications Of Dielectrophoresis In Biotechnology," Tibtech, vol. 15, pp. 426-432, Oct. 1997.

Protana website, "NanoES Products," www.protana.com/products/default.asp, 3 pages, Sep. 19, 2000.

Qin, Dong et al., "Elastomeric Light Valves," Adv. Mater., vol. 9, No. 5, pp. 407-410, 1997.

Qin, Dong et al., "Photolithography With Transparent Reflective Photomasks," J. Vac. Sci. Technol. B, vol. 16, No. 1, pp. 98-103, Jan. 1998.

Quake, Stephen R. et al., "From Micro- To Nanofabrication With Soft Materials," Science, vol. 290, pp. 1536-1540, Nov. 24, 2000.

Rapp, R. et al., "LIGA Micropump For Gases And Liquids," Sensors and Actuators A, vol. 40, pp. 57-61, Jan. 1994.

Roylance, Lynn Michelle et al., "A Batch-Fabricated Silicon Accelerometer," IEEE Transactions on Electron Devices, vol. ED-26, No. 12, pp. 1911-1917, Dec. 1979.

Sandia National Laboratories, "Electro Microfluidic Dual In-Line Package (EMDIP)," 2 pages, no date.

Sanjoh, Akira et al., "Spatiotemporal Protein Crystal Growth Studies Using Microfluidic Silicon Devices," Journal of Crystal Growth, vol. 196, pp. 691-702, 1999.

Sasserath, J. et al., "Rapid Prototyping And Development Of Microfluidic And BioMEMS Devices," IVD Technology, 12 pages, Jun. 2002.

Schasfoort, Richard B. M. et al., "Field-Effect Flow Control For Microfabricated Fluidic Networks," Science, vol. 286, pp. 942-945, Oct. 29, 1999.

Schomburg, W. K. et al., "Fabrication Of Polymer Microcomponents With The AMANDA-Process," New Materials and Directions, Eurosensors XII, pp. 711-714, Sep. 13-16, 1998.

Schueller, Olivier J. A. et al., "Fabrication Of Glassy Carbon Microstructures By Soft Lithography," Sensors and Actuators A, vol. 72, pp. 126-139, 1999.

Shevchenko, Andrej et al., "Rapid 'de Novo' Peptide Sequencing By A Combination Of Nanoelectrospray, Isotopic Labeling And A Quadrupole/Time-Of-Flight Mass Spectrometer," Rapid Communications in Mass Spectrometry, vol. 11, pp. 1015-1024, 1997.

Shinohara, Jun et al., "A High Pressure-Resistance Micropump Using Active And Normally-Closed Valves," IEEE, pp. 86-91, 2000.

Shoji, Shuichi, "Fluids For Sensor Systems," Topics in Current Chemistry, vol. 194, pp. 163-188, 1998.

Shoji, Shuichi et al., "Smallest Dead Volume Microvalves For Integrated Chemical Analyzing Systems," Transducers '91, 1991 International Conference on Solid-State Sensors and Actuators, San Francisco, California, pp. 1052-1055, 1991.

Smits, J.G., "Piezoelectric Micropump With Three Valves Working Peristaltically," Sensors and Actuators, vol. A21-A23, pp. 203-206, 1990.

Sohn, L. L. et al., "Capacitance Cytometry: Measuring Biological Cells One By One," PNAS, vol. 97, No. 20, pp. 10687-10690, Sep. 26, 2000.

Thompson, L. F. et al., "Introduction To Microlithography," 185th Meeting of the American Chemical Society, Seattle, WA, pp. 2 cover pages, 1-13, Mar. 20-25, 1983.

Thorsen, Todd et al., "Dynamic Pattern Formation In A Vesicle-Generating Microfluidic Device," Physical Review Letters, vol. 86, No. 18, pp. 4163-4166, Apr. 30, 2001.

Todd, Paul et al., "Chapter 12—Cell Electrophoresis," Flow Cytometry and Sorting, John Wiley & Sons, pp. 5 cover pages and 217-229, 1979.

Tufte, O. N. et al., "Silicon Diffused-Element Piezoresistive Diaphragms," Journal of Applied Physics, vol. 33, No. 11, pp. 3322-3327, Nov. 1962.

Ullmann's Encyclopedia of Industrial Chemistry, Sections 6 to 6.3, Topic: Carbon Black; Sixth Edition, 7 pages, 1999.

Unger, Marc A. et al., "Monlithic Microfabricated Valves And Pumps By Multilayer Soft Lithography," Science, vol. 288, pp. 113-116, Apr. 7, 2000.

Van de Pol, F.C.M. et al., "A Thermo-Pneumatic Actuation Principle For A Microminiature Pump And Other Micromechanical Devices," Sensors and Actuators, vol. 17, Nos. 1-2, pp. 139-143, May 3, 1989.

Van de Pol, F.C.M. et al., "Micro Liquid Handling Devices—A Review," Micro Systems Technologies, vol. 90, pp. 799-805, 1990.

Van Den Berg, A. et al., "Micro Total Analysis Systems," Proceedings of the µTAS '94 Workshop, University of Twente, The Netherlands, 17 pages, Nov. 21-22, 1994.

Van Der Woerd, Mark et al., "Lab-On-A-Chip Based Protein Crystallization," National Aeronautics and Space Administration and Caliper, pp. 1-27, Oct. 25, 2001.

Verpoorte, Elisabeth M. J. et al., "Three-Dimensional Micro Flow Manifolds For Miniaturized Chemical Analysis Systems," J. Micromech. Microeng., vol. 7, pp. 246-256, 1994.

Vieider, Christian et al., "A Pneumatically Actuated Micro Valve With A Silicon Rubber Membrane For Integration With Fluid Handling Systems," Transducers '95, 8th International Conference on Solid-State Sensors and Actuators and Eurosensors IX, Stockholm, Sweden, pp. 284-286, Jun. 25-29, 1995.

Volkmuth, W. D. et al., "DNA Electrophoresis In Microlithographic Arrays," Nature, vol. 358, pp. 600-602, Aug. 13, 1992.

Washizu, Masao et al., "Molecular Dielectrophoresis Of Biopolymers," IEEE Transactions on Industry Applications, vol. 30, No. 4, pp. 835-843, Jul. 1994.

Weigl, Bernhard H., "Microfluidics-Based Lab-On-A-Chip Systems," IVD Technology Magazine, 8 pages, Nov./Dec. 2000.

Whitesides, George M. et al., "Flexible Methods For Microfluidics," Physics Today, pp. 42-48, Jun. 2001.

Whitesides, George M. et al., "Soft Lithography In Biology And Biochemistry," Annu. Rev. Biomed. Eng., vol. 3, pp. 335-373, 2001.

Wilbur, James L. et al., "Lithographic Molding: A Convenient Route To Structures With Sub-Micrometer Dimensions," Adv. Mater., vol. 7, No. 7, pp. 649-652, 1995.

Wilm, Matthias et al., "Femtomole Sequencing Of Proteins From Polyacrylamide Gels By Nano-Electrospray Mass Spectrometry," Nature, vol. 379, pp. 466-469, Feb. 1, 1996.

Xia, Younan et al., "Complex Optical Surfaces Formed By Replica Molding Against Elastomeric Masters," Science, vol. 273, pp. 347-349, Jul. 19, 1996.

Xia, Younan et al., "Micropumping Of Polymers In Capillaries: Applications In Microfabrication," Chem. Mater., vol. 8, No. 7, pp. 1559-1566, 1996.

Xia, Younan et al., "Reduction In The Size Of Features Of Patterned SAMs Generated By Microcontact Printing With Mechanical Compression Of The Stamp," Adv. Mater., vol. 7, No. 5, pp. 471-473, 1995.

Xia, Younan et al., "Soft Lithography," Angew. Chem. Int. Ed., vol. 37; pp. 551-575, 1998.

Xu, Bing et al., "Making Negative Poisson's Ratio Microstructures By Soft Lithography," Adv. Mater., vol. 11, No. 14, pp. 1186-1189, 1999.

Xu, Jingdong et al., "Room-Temperature Imprinting Method For Plastic Microchannel Fabrication," Analytical Chemistry, vol. 72, No. 8, pp. 1930-1933, Apr. 15, 2000.

Xue, Qifeng et al., "Integrated Multichannel Microchip Electrospray Ionization Mass Spectrometry: Analysis Of Peptides From On-Chip Tryptic Digestion of Melittin," Rapid Communications In Mass Spectrometry, vol. 11, 1253-1256, 1997.

Xue, Qifeng et al., "Multichannel Microchip Electrospray Mass Spectrometry," Analytical Chemistry, vol. 69, No. 3, pp. 426-430, Feb. 1, 1997.

Yang, Xing et al., "A Low Power MEMS Silicone/Parylene Valve," Solid-State Sensor and Actuator Workshop, Hilton Head Island, South Carolina, 4 pages, Jun. 7-11, 1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Young, A. M. et al., "Contoured Elastic-Membrane Microvalves For Microfluidic Network Integration," Journal of Biomechanical Engineering, vol. 121, pp. 2-6, Feb. 1999.

Zengerle, R. et al., "A Micro Membrane Pump With Electrostatic Actuation," Micro Electro Mechanical Systems '92, Travemünde, Germany, pp. 19-24, Feb. 4-7, 1992.

Zengerle, R. et al., "Performance Simulation Of Microminiaturized Membrane Pumps," 7th International Conference on Solid-State Sensors and Actuators, Yokohama, Japan, pp. 2 cover pages, 106-109, Jun. 7-10, 1993.

Zhang, B. et al., "Microfabricated Devices For Capillary Electrophoresis-Electrospray Mass Spectrometry," Analytical Chemistry, vol. 71, No. 15, pp. 3258-3264, Aug. 1, 1999.

Zhao, Zhan, et al., "An Integrated Biochip Design and Fabrication," Proceedings of SPIE, vol. 4936, pp. 321-326, 2002.

Barron, Annelise E., *Capillary Electrophoresis of DNA in Uncross-Linked Polymer Solutions* (1993) Journal of Chromatography A 652(1): 3-16.

Barron, Annelise, *The Use of Coated and Uncoated Capillaries for the Electrophoretic Separation of DNA in Dilute Polymer-Solutions* (1995) Electrophoresis 16(1):64-74.

Barron, A.E., *DNA Separations by Slab Gel and Capillary Electrophoresis—Theory and Practice* (1995) Separation and Purification Methods 24:1-118.

Effenhauser, C.S., *Miniaturizing a Whole Analytical Laboratory Down to Chip Size* (1994) American Laboratory 26(14):15.

Effenhauser, C.S., *Integrated Capillary Electrophoresis on Flexible Silicone Microdevices: Analysis of DNA Restriction Fragments and Detection of Single DNA Molecules on Microchips* (1997) Analytical Chemistry 69(17):3451-3457.

Effenhauser, C.S., *Integrated Chip-Based Microcolumn Separation Systems* (1998) Microsystem Technology in Chemistry and Life Science 194:51-82.

Felix, A.M., *Peglated Peptides .4. Enhanced Biological-Activity of Site-Directed Pegylated Grf Analogs* (1995) International Journal of Peptide and Protein Research 46(3-4):253:264.

Felix, A.M. *Site-Specific Poly(ethylene glycol)ylation of Peptides* (1997) Poly(Ethylene Glycol) 680:218-238.

Gombotz, W.R., Pegylation: *A Tool to Enhance Protein Delivery* (1999) Abstracts of Papers of the American Chemical Society 217:U528-U5282.

Guerra, P.I., *PEGylation Prevents The N-Terminal Degradation of Megakaryoocyte Growth and Development Factor* (1998) 15(12) 1822-1827.

Kodera, Y., *Pegylation of Proteins and Bioactive Substances for Medical and Technical Applications* (1998) Progress in Polymer Science 23(7): 1233-1271.

Lee, L.S., *Prolonged Circulating Lives of Single-Chain Fv Proteins Conjugated with Polyethyelene Glycol: A Comparison of Conjugation Chemistries and Compounds* (1999) Bioconjugate Chemistry 10(6): 973-981.

Menchen, S., *Flowable Networks as DNA Sequencing Media in Capillary Columns* (1996) Electrophoresis 17(9): 1451-1459.

Veronese, F.M., *Influence of PEGylation on the Release of Low and High Molecular-Weight Proteins from PVA Matrices* (1999) Journal of Bioactive and Compatible Polymers 14(4): 315-330.

Veronese, F.M., Peptide and Protein PEGylation: A Review of Problems and Solutions (2001) Biomaterials 22(5): 405-417.

Wu,, C.H., *Viscosity-adjustable Block Coploymer for DNA Separation by Capillary Electrophoresis* (1998) Electrophoresis 19(2):231-241.

Zalipsky, S. *Chemistry of Polyethyelene-Glycol Conjugates with Biologically-Active Molecules* (1995) Advanced Drug Delivery Reviews 16(2-3): 157-182.

* cited by examiner

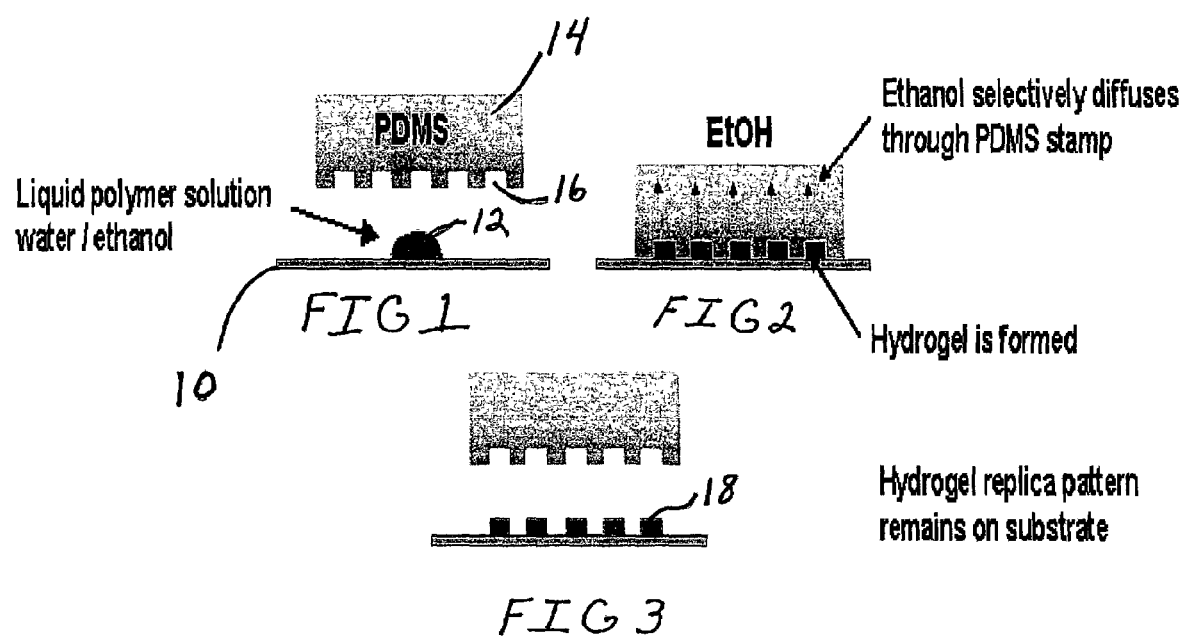

DEVICES UTILIZING SELF-ASSEMBLED GEL AND METHOD OF MANUFACTURE

CROSS-REFERENCE

This application claims priority from provisional application Ser. No. 60/328,595, filed on Oct. 11, 2001, which is incorporated herein by reference.

GOVERNMENT RIGHTS

This invention was made with government support under grant numbers DMR-0080065 & CTS-9729443 awarded by the National Science Foundation and by grant number DAAD19-00-1-0392 awarded by DARPA. The government has certain rights in the invention.

BACKGROUND

Devices containing gels, such as microfluidic devices, find use in many analytical detection techniques. For example, capillary electrophoresis is used for DNA profiling, analysis of pharmaceuticals, and detection and analysis of proteins and peptides.

A typical capillary for capillary electrophoresis is made of glass. Also used are polymeric materials, such as poly (dimethylsiloxane) ("PDMS") silicone elastomer. The use and fabrication of PDMS devices are described by Effenhauser et al., "Integrated Capillary Electrophoresis on Flexible Silicone Microdevices: Analysis of DNA Restriction Fragments and Detection of Single DNA Molecules on Microchips", *Anal. Chem.* (1997) 69, 3451–3457 which is incorporated herein by reference. An advantage of polymeric materials is fabrication costs are less than the fabrication costs with glass, and thus arrays of capillaries in a detection device or on a chip can be fabricated at lower cost with elastomers than glass. However, a limitation on use of PDMS and other polymeric material capillaries is they have less structural strength than glass.

Because of the lower structural strength of some polymeric capillaries, they cannot be used with high viscosity gels, because high pressures are required to introduce the gel into a microchannel. Thus many polymeric capillaries are limited to use with low viscosity gels or linear polymers as the separation fluid. High viscosity gels have advantages in some applications, particularly where high resolution is needed. For example, low viscosity gels are not effective for DNA sequencing on microchips, because high base-pair resolution is needed with relatively short separation channels, which requires a high viscosity gel.

Attempts have been made to form high viscosity gels in situ, starting with a low viscosity liquid. For example, chemically cross-linked gels have been used in capillary electrophoresis. However, in situ chemically cross-linked gels are difficult to fabricate inside capillaries, partly due to the shrinkage that occurs during the cross-linking reaction. In addition, the cross-linking chemistry includes an additional step in fabrication of the device, which increases cost. Furthermore, the gelation is irreversible, i.e., a matrix cannot be replaced after the formation of the gel.

An attempt was made to use temperature control to form a high viscosity gel in situ from a gel precursor with low viscosity. The gel precursor was designed so that a temperature change yields a high viscosity gel. See, Wu, C. H. et al. (1998), "Viscosity-Adjustable Block Copolymer for DNA Separation by Capillary Electrophoresis." *Electrophoresis* 19(2):231–241. However, this techniques requires temperature control during the fabrication process, and results in a limited temperature range in which the device can be used. If the temperature changes, the gel can change properties and even become very fluid.

Accordingly, there is a need for an easy method of fabricating devices utilizing a high viscosity gel, without the need for the fabrication pressures associated with high viscosity gels, and where the device does not have a narrow temperature range in use.

SUMMARY

The present invention satisfies this need with a unique low viscosity gel precursor that can easily be converted to a high viscosity self-assembled gel without any temperature change required. The gel precursor is formed from a water soluble polymer having hydrophobic moieties, typically hydrophobic end groups. In its low viscosity gel precursor state, the water soluble polymer is in a solvent mixture comprising water and an organic solvent, where in the absence of the organic solvent, the polymer forms a self-assembled gel. The gel precursor contacts a substrate that comprises a permeable material that has higher permeability for the organic solvent than water. The organic solvent diffuses through the permeable material, resulting in formation of the self-assembled gel. A preferred permeable material is PDMS silicone elastomer.

In one version of the invention, a microfluidic device such as a capillary for capillary electrophoresis can be made at least partly of the permeable material, and when the self-assembling gel is introduced into the capillary, the organic solvent diffuses through the permeable material, and the self-assembled gel forms.

In another version of the invention, the self-assembling gel precursor is placed on a first substrate which is substantially hydrophobic which can be substantially non-permeable. The precursor is then contacted with a second substrate comprising a permeable material such as PDMS, resulting in the formation of the self-assembled gel on the first substrate. If the second substrate has a plurality of holes or voids in it, the resulting product can be an array of separated regions containing the self-assembled gel formed on the first substrate.

A reagent, such as a biopolymer, can be immobilized in the gel. The reagent can be an enzyme so that gel can be used for enzymatic reactions, or an antibody for detecting a particular antigen.

Thus, according to the present invention, devices having a high viscosity gel, with or without an immobilized reagent, can easily be fabricated because a low viscosity gel precursor is used.

DRAWINGS

These and other features, aspects and advantages of the present invention will become better understood with reference to the following description, appended claims, and accompanying drawings where FIGS. 1–3 schematically show the formation of self-assembled gel regions on a substrate.

DESCRIPTION

The present invention utilizes gel precursors, also known as self-assembling gels, that upon a change in solvent composition, form a self-assembled gel.

The gel precursor is made of a water-soluble hydrophilic polymer modified with hydrophobic groups. Suitable gels are described by Menchen et al., "Synthesis, Characterization, and Rheological Behavior of Polyethyelene Glycols End-Capped with Fluorocarbon Hydrophobes", (1997), 13, 2447–2456, which is incorporated herein by reference. The method taught by Menchen et al. can be used to form the gel precursor.

Exemplery of suitable water-soluble hydrophilic polymers and poly(ethylene glycol) ("PEG"), poly(vinyl alcohol), poly(vinyl pyrrolidone), are poly(acrylamide).

The molecular weight of the polymer is sufficiently high to form a gel, but sufficiently low that the gel precursor is a low viscosity fluid. The polymer before modification with a hydrophobic group generally has a molecular weight of at least 2,000, and generally up to about 100,000.

The hydrophobic moiety is usually attached to the hydrophilic polymer as an end group, but it need not be. Preferably there is a hydrophobic group at each end of the hydrophilic polymer.

The hydrophobic moiety can be an alkyl group, which preferably is fluorinated, and most preferably is fully fluorinated. Exemplary of suitable compounds for attachment to PEG to yield an attached hydrophobic moiety are branched $C_nF_{2n+1}C_mH_{2m}O$—; $C_mH_{2m+1}O$)—; or short blocks of a hydrophobic polymer such as polystyrene polyisoprene, polybutadiene or their hydrogenated or fluorinated analogues. Typically n can be 6 and m can be 2.

Generally only one type of hydrophobic group is used, although in some circumstances, different hydrophobic groups can be used with the hydrophilic polymer.

The solvent mixture used contains water and at least one organic solvent that is miscible with water and is capable of dissolving the end group. Generally, a polar solvent is used. Solvents that can be used include methanol, ethanol, N-methylpyrollidone, and tetrahydrofuran. Generally, only one organic solvent is used, but more than one can be used.

To prevent premature gelation and to have a low viscosity, preferably the concentration of the modified polymer in the solvent is less than 20%, and it can be as low as 1% by weight.

There needs to be sufficient organic solvent in the solvent mixture to prevent premature gelation. It is found that a 50%/50% by weight mixture is satisfactory.

By removal of the organic solvent, a self-assembled, high viscosity gel is formed. The self-assembled gel has a viscosity of at least about 20 Pa s at low shear rates. This occurs when about 90% of the organic solvent is removed. Generally, it is preferred that substantially all of the organic solvent is removed to form a homogeneous hydrogel. Removal is effected with a permeable material that is substantially more permeable to the organic solvent than to water. The permeable material selectively removes the organic solvent(s) from the solvent mixture. Preferably, the permeability of the organic solvent through the permeable material is at least five times greater than the permeability of water through the permeable material. A suitable permeable material is PDMS silicone elastomer. Other suitable materials are polymethylmethacrylate and polycarbonate. A polyolefin elastomer, a polyurethane, a Kraton-type thermoplastic elastomer, or polynorbornene can be suitable, particularly if the organic solvent is non-polar.

Thus, by contacting the gel precursor with PDMS silicone elastomer, a self-assembled gel is formed. This occurs quickly and can occur in just a few minutes at room temperature and ambient pressure within gaps, channels or voids.

Preferably the gel precursor contains no constituents that interfere with the performance of the formed gel. For example, for capillary electrophoresis, it is desirable to have a homogenous gel, and thus preferably the gel precursor contains no electrolytes that are attached to the polymer that can interfere with the performance of the gel as a separation medium for capillary electrophoresis.

Different types of articles can be made utilizing the gel precursor. In one type of article, the permeable material forms part of the finished article. In another type of article, the permeable material is not part of the finished article, but is only used to manufacture the article.

Exemplary of the first type are microfluidic devices, such as capillaries. The term "capillaries" is used to refer to a structure having at least one dimension smaller than about 200 microns. Capillaries typically have diameters of from 10 to about 200 microns, and can have a length as long as 50 cm. Exemplary of such devices are flexible silicone microdevices described in the aforementioned Effenhauser et al. article. The gel precursor is introduced, such as by a syringe, into the channels of the device. The organic solvent diffuses out through the permeable material, resulting in formation of the self-assembled hydrogel.

It is not necessary that the entire device be formed of the permeable material. All that is necessary is that there may be some permeable material in contact with the gel precursor, so that the organic solvent can diffuse out of solution.

In the second type of device, the substrate on which the gel is formed need not be a permeable material. For example, the precursor gel can be placed on a first substrate made of substantially non-permeable hydrophobic material, such as a glass plate. Then a second substrate comprising a permeable material is placed in contact with the gel precursor, resulting in the formation of the gel. For example, a stamp having voids therein can be used to print patterns of hydrogel on a surface of the first substrate. The stamp can be made of PDMS, and can be pressed down on the glass surface having the gel precursor. The gel precursor is pressed into the voids, and as the solvent diffuses through the PDMS, gel is formed in the voids. This results in the first substrate having multiple separated regions of gel thereon. The regions can be in the form of an array.

For example, as shown in FIGS. 1–3, a substrate 10 such as glass that has been silanized has a gel precursor 12 placed thereon, and is then pressed with a stamp 14 having a plurality of voids 16 or holes therein. The stamp 14 is made of PDMS. The organic solvent in the gel precursor diffuses from the gel precursor solution, resulting in the formation of gel regions 18 where the voids 16 are located.

Biopolymers can be incorporated into the gel. The term "biopolymers" is meant to include all molecules of biological interest, such as catalysts; drugs; DNA; RNA; and peptides and proteins, including antibodies, ligands, receptors and enzymes.

A biopolymer can be incorporated by physical entrapment or modified for incorporation into the gel through "pegylation" reactions such as those described by Veronese, F. N. (2001) "Peptide and Protein PEGylation: A review of Problems and Solutions," *Biomaterials,* 22(5): 405–417; and Zalipsky, S. (1995), "Chemistry of Polyethylene-Glycol Conjugates with Biologically-Active Molecules," *Advanced Drug Delivery Reviews* 16(2–3): 157–182, both of which documents are incorporated herein by reference.

A hydrophilic polymer coupled to at least one hydrophobe may be coupled to one or more biopolymers. The resulting conjugate comprising (i) at least one hydrophilic polymer, (ii) at least one hydrophobic moiety group, and (iii) at least one biopolymer, can be linked and immobilized to the hydrogel network by the aggregation of the attached hydrophobic moiety. One route to an exemplary biopolymer conjugate is as follows. When a biopolymer is to be incorporated into the network, a reagent comprising a hydrophilic polymer with a single hydrophobe can be obtained by reacting a hydrophilic polymer with an amount of hydrophobic moiety in the order of about equivalent with respect to the mount of hydrophilic polymer chains, so that some of the hydrophilic polymer chains have only one hydrophobic end group. By a fractionation process as exemplified in the Examples section below, the polymer is divided into three fractions, those with two hydrophobic end groups, those with one hydrophobic end group, and those with no hydrophobic end groups. The fraction with no hydrophobic end groups is discarded. The fraction with one hydrophobic end group is bound to a biopolymer.

The immobilized biopolymer species can serve many functions, depending on the particular biopolymer. For example, if the biopolymer is an enzyme, the gel can serve as a microreactor for in column digestion. If the biopolymer is an antibody, it can be used for specific binding of a particular antigen. If it is a ligand it can be used for chromatography for a particular receptor. If it is a receptor, it can be used to screen potential drugs for their binding affinity.

The present invention has significant advantages. For example, it is possible to fabricate a microfluidic device inexpensively due to the low viscosity nature of the gel precursor, and its ability to be used with polymeric substances. The invention provides an inexpensive way of forming an array on a chip. Moreover, the self-assembled gel can easily be removed from devices, or the configuration of the gel can be changed, merely by introducing the organic solvent, resulting in the self assembled gel reforming into a gel precursor having a low viscosity state.

EXAMPLES

Example 1

Synthesis of Hydrophobic End-Functionalized PEG.

This procedure is similar to ones reported in literature; namely Xu, L. Li, A. Yekta, Z. Masoumi, S. Kanagalingam, M. A. Winnik, K. Zhang, P. M. Macdonald, S. Menchen, *Langmuir* (1997) 13, 2447, which is incorporated herein by reference. The general reaction scheme for synthesizing PEG with fluoralkyl groups on both chain ends is as follows:

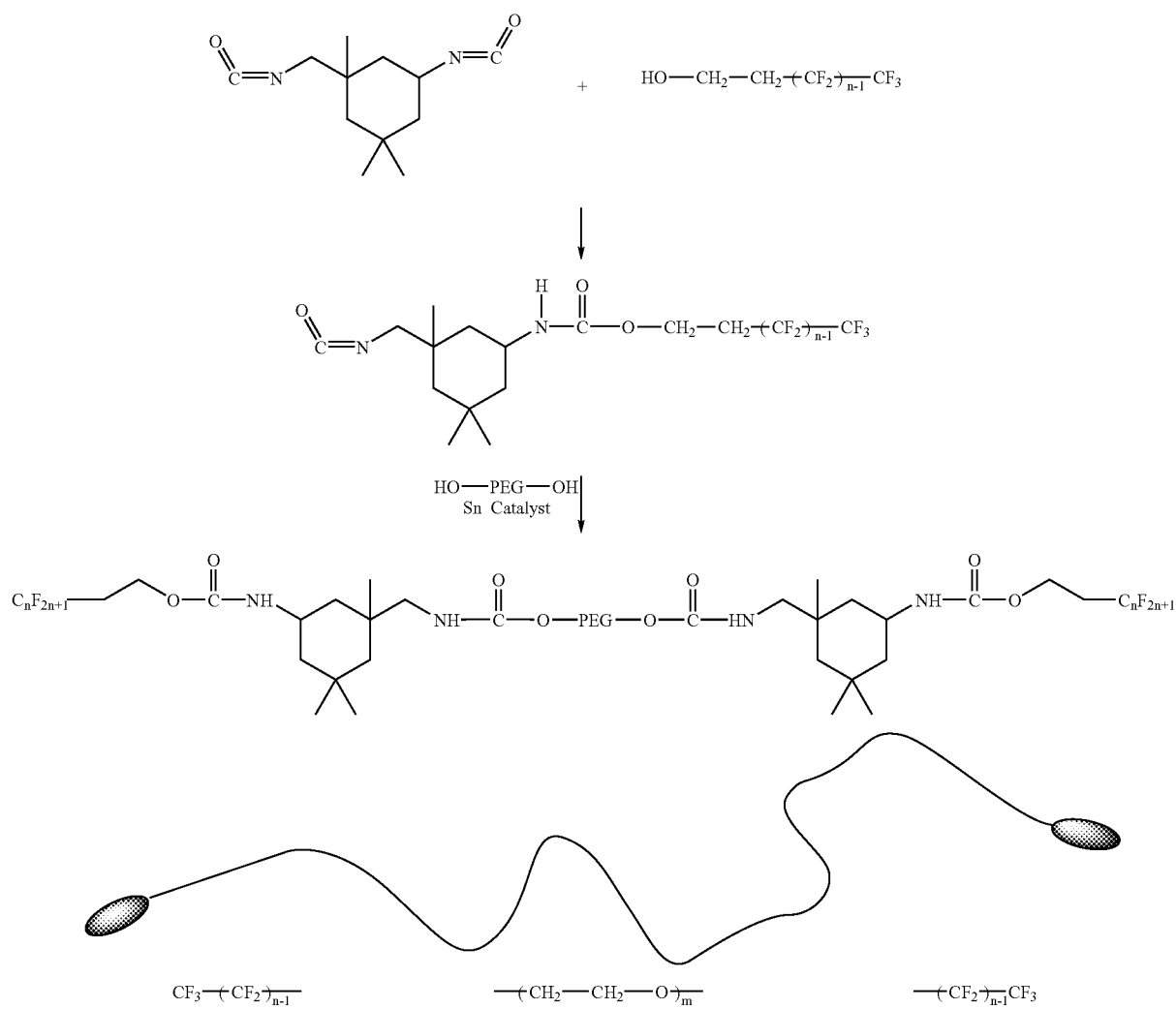

Perfluoroalcohols were reacted with an excess of isophorone diisocyanate (IPDI) linker. The excess IPDI was distilled of at 130° C. under vacuum. Then the hydrophobes were recrystallized four times in hexanes at −20° C.

For the synthesis of the hydrophobic end-functionalized PEG, an excess of hydrophobes were reacted with the PEG (MW=6,000 to 35,000), so that almost complete substitution of the PEG end-groups was obtained (both end groups modified with a hydrophobe). For the synthesis of a monofunctional hydrophobically modified PEG, the hydrophobes were reacted with PEG (MW=6, 000 in a 1:1 ratio (1 hydrophobe per PEG chain). The reaction was performed at 75° C. in ethyleneglycol dimethylether or tetrathydrofuran, with the addition of a few drops of dibutyltinlaureate as a catalyst. The product was precipitated in cold diethylether.

Typically the reaction for synthesizing the PEG substituted with a single hydrophobe gave a mixture of unmodified PEG, PEG with a single hydrophobe, and PEG with two hydrophobes. The product can be analyzed by HPLC (conditions: linear gradient: $H_2O/CH_3CN$; 70/30 to 0/100 in 70 minutes. 20 microliter injected, C18 column, evaporative mass detector).

The product of interest was isolated by a fractionation procedure as follows. First the product was dissolved in ethyl acetate by slightly heating. Then it was allowed to recrystallize at room temperature for two days. The precipitate (unreacted PEG) was filtered off and the solution was stored at 4° C. overnight. A small amount of precipitate formed (PEG with single hydrophobe) which was filtered from the solution and dried in vacuum. Since only a small amount of product can be recovered each cycle by this procedure, it was repeated several times, until the desired amount of product has been recovered. The product was analyzed by HPLC.

Example 2

Activation of the PEG with Single Hydrophobe.

The product of Example 1 that has one end of the PEG bearing the hydrophobe of interest, with the other end being alcohol is being used for activation. Activation of the alcohol end can be done by a variety of routes that have been described in the literature; for example, by using procedures described by F. M. Veronese, *Biomaterials* (2001), 22, 405, which is incorporated herein by reference. The general reaction scheme used is as follows:

The activation rendered the end group of PEG reactive towards amines. This molecule was suitable for PEGylation reactions with biopolymers.

Example 3

Fabrication of Microchannels.

A microfluidic device having microchannels was fabricated by pouring prepolymer on a silicon wafer mold containing positive-relief channels patterned in photoresist, which was then cured. The channels were fully encapsulated by curing the patterned polymer matrix material on a coverslip coated with a thin layer of polymer matrix material and bonding the two layers together through an additional cure. The procedure is similar to that described in the literature for multilayer soft lithography, namely M. A. Unger, H. P. Chou, T. Thorsen, A. Scherer, S. R. Quake, *Science* (2000), 288, 133, which is incorporated herein by reference.

Example 4

Filling of Microchannels with Hydrogel.

The hydrogel forming material from Example 1 with two hydrophobes on each PEG chain (e.g. a 10,000 PEG chain modified with two $C_8F_{17}$ end groups) was dissolved in a $H_2O$/Alcohol (either methanol or ethanol) mixture. Already at fairly low alcohol fractions approximately 10% alcohol or more, the solution was liquid-like, and could be injected with a syringe into the microchannels. Gelation was complete as soon as the alcohol diffused out of the microchannels, which took a few minutes.

Example 5

Fabrication of Stamps.

Stamps were prepared by replica molding by casting the liquid prepolymer of an elastomer against a master that had a patterned relief structure in its surface, according to the technique of Y. Xia, G. M. Whitesides, Angew. *Chem. Int.*

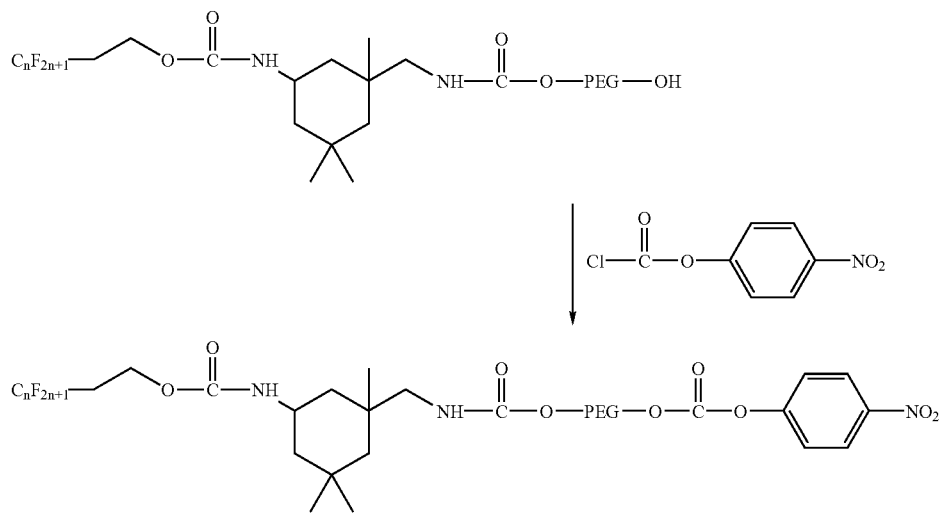

Ed. 1998, 37, 550, which is incorporated herein by reference. The elastomer used was poly(dimethylsiloxane) (PDMS).

Example 6

Hydrogel Array Manufacture.

An array was formed as shown in FIGS. 1–3. Hydrogel forming material prepared by the method of Example 1 (PEG end-modified with two hydrophobes per PEG chain, e.g. PEG MW 6,000 with two $C_{10}F_{21}$ ends) was dissolved in an $H_2O$/Alcohol (ethanol or methanol) mixture (1/1) at approximately 0.5–2 wt %.

A drop of the solution, consisting of the hydrogel forming material in a $H_2O$/alcohol mixture, was placed on a glass slide or silicon wafer that was previously silanized with a perfluoro silane e.g. trichloro (1H, 1H, 2H, 2H perfluorooctyl) silane. After placing a drop of the polymer solution onto the substrate, the stamp of Example 5 was placed onto the drop. After leaving the stamp and substrate in contact overnight, the stamp was removed from the substrate, leaving the pattern of the hydrogel forming material behind in an array.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. § 112.

Although the present invention has been described in considerable detail with reference to the preferred versions thereof, other versions are possible, Therefore the scope of the appended claims should not be limited to the descriptions of the preferred versions contained therein.

What is claimed is:

1. An article of manufacture comprising:
   a) a capillary comprising a permeable material that has higher permeability for organic solvents than for water; and
   b) a separation medium comprising a reversible self-assembled gel that is formed in the capillary from precursor materials comprising an organic solvent, water, and a water soluble polymer with hydrophobic moieties, wherein the reversible self-assembled gel is formed as the organic solvent diffuses through the permeable material of the substrate capillary, and wherein the precursor materials have a lower viscosity than the reversible self-assembled gel, and
   wherein the article is formed as one or more capillaries filled with the separation medium suitable for use in capillary electrophoresis, and wherein separation medium slows migration of an analyte through the capillaries.

2. The article of manufacture of claim 1 wherein the water soluble polymer is a linear water soluble polymer bearing hydrophobic end groups.

3. The article of manufacture of claim 1 where the hydrophobic moieties are end groups.

4. The article of claim 1 comprising a reagent immobilized in the gel.

5. The article of claim 4 wherein the reagent is attached to the water soluble polymer.

6. The article of claim 4 wherein the reagent is embedded in the gel.

7. The article of claim 4 wherein the reagent is a biopolymer.

8. The article of claim 1 wherein the permeable material is a polymer.

9. The article of claim 1 wherein the permeable material is poly(dimethylsiloxane) silicone elastomer.

10. The article of claim 1, wherein the one or more capillaries comprises an array of capillaries suitable for use in capillary electrophoresis.

11. The article of claim 1, wherein the reversible self-assembled gel is reformed back into the precursor materials by introducing more of the organic solvent into the capillary.

* * * * *

UNITED STATES PATENT AND TRADEMARK OFFICE
CERTIFICATE OF CORRECTION

PATENT NO. : 7,192,629 B2 Page 1 of 1
APPLICATION NO. : 10/269475
DATED : March 20, 2007
INVENTOR(S) : Lammertink et al.

It is certified that error appears in the above-identified patent and that said Letters Patent is hereby corrected as shown below:

On the Title Page, under Other Publications, page 2, Item 56, line 70, delete "Bearn" and insert --Beam--;

On the Title Page, under Other Publications, page 2, Item 56, line 23, delete "Mycornetrix:" and insert --Mycometrix:--;

On the Title Page, under Other Publications, page 2, Item 56, line 23, delete "Carclina" and insert --Carolina--;

On the Title Page, under Other Publications, page 3, Item 56, line 55, delete "vol. 83" and insert --vol. 63--;

On the Title Page, under Other Publications, page 4, Item 56, line 43, delete "Piezoelectric" and insert --Plezoelectric--.

Signed and Sealed this

Seventeenth Day of June, 2008

JON W. DUDAS
*Director of the United States Patent and Trademark Office*